United States Patent [19]
Goldenberg et al.

[11] Patent Number: 5,736,348
[45] Date of Patent: Apr. 7, 1998

[54] METHOD FOR THE IMMUNOLOGICAL DIAGNOSIS OF CHAGAS' DISEASE USING RECOMBINANT ANTIGENS

[75] Inventors: Samuel Goldenberg; Marco Aurélio Krieger; Elza Carmen Cerqueira De Almeida, all of Rio De Janeiro, Brazil

[73] Assignee: Fundacao Oswaldo Cruz (Fiocruz), Rio de Janeiro, Brazil

[21] Appl. No.: 392,623

[22] Filed: Feb. 22, 1995

Related U.S. Application Data

[63] Continuation of Ser. No. 916,073, filed as PCT/BR91/00027, Nov. 28, 1991, published as WO92/09895, Nov. 6, 1992, abandoned.

[30] Foreign Application Priority Data

Nov. 28, 1990 [BR] Brazil ..................................... 9006039

[51] Int. Cl.[6] ..................... G01N 33/535; G01N 33/569; G01N 33/543
[52] U.S. Cl. .......................... 435/7.92; 436/518; 436/811
[58] Field of Search ...................... 435/7.22, 7.3, 435/7.92, 7.4, 810, 970, 975; 436/518, 811

[56] References Cited

FOREIGN PATENT DOCUMENTS 0273555  6/1988  European Pat. Off. .
92/09895  6/1992  WIPO .

OTHER PUBLICATIONS

Groeneveld, R.A., "An Introduction to Probability and Statistics Using Basic", Marcel Dekker, Inc., N.Y., pp. 377–382 (1979).

Krieger et al., "Use of Recombinant Antigens for the Accurate Immunodiagnosis of Chagas'Disease", Am. J. Trop. Med. Hyg. 46(4):427–434 (1992).

A.O. Luquetti, "Use of Trypanosoma cruzi defined proteins for diagnosis–multicentre trial serological and technical aspects", Mem. Inst. Oswaldo Cruz, Rio de Janeiro, vol. 85(4): 497–505, Feb. 7 1991.

A. Moncayo & A.O. Luquetti, "Multicentre double blind study for evluation of Trypanosoma cruzi defined antigens as diagnostic reagents", Mem. Inst. Oswaldo Cruz, Rio de Janeiro, vol. 85(4): 489–495, Feb. 7, 1991.

Levin, et al., "Autoantibodies in Chagas'Heart Disease: Possible Markers of Severe Chagas'Heart Complaint" Mem. Inst. Oswaldo Cruz, Rio de Janeiro, vol. 85(4): 539–543, Oct./Dec. 1990.

Seebeck, et al., "The Cytoskeleton of Trypanosomes", Parasitology Today, vol. 6, No.2, pp. 49–52, 1990.

Enzyme–Immunoassay, Appendix 4, An Example of the Indirect Microplate Elisa, 1980, p. 194.

Krieger et al., Use of recombinant antigens for the immunological diagnosis of Chagas disease, Mem. Inst. Oswaldo Cruz 85 (Suppl. I), 54, 1990.

Harlow et al., Antibodies A Labortory Manual. Cold Spring Harbor Laboratory, 1988. p. 348; p.592.

La faille et al., Structure and expression of two *Tryanosoma Crugi* genes encoding antigenic proteins bearing repetitive epitopes. Molec and Biochem. Parasitol. 35: 127–136. 1989.

Odell et al., Eds, Principles of Competitive Protein–Binding Assays. John Wiley & Sons, New York, 1971, pp. 243–254.

*Primary Examiner*—Marian C. Knode
*Assistant Examiner*—Donna C. Wortman
*Attorney, Agent, or Firm*—Cushman Darby & Cushman IP Group of Pillsbury Madison & Sutro LLP

[57] ABSTRACT

This patent deals with the use of *Trypanosoma cruzi* antigens obtained using recombinant DNA techniques, or synthetic peptides derived from these antigens, and their use in the immunological diagnosis of Chagas Disease using either ELISA, or western blot, or dot-blot, or hemagglutination, or agglutination, or monoclonal antibodies, or radioimmunoassay. The antigens or synthetic peptides are characterized by displaying the following aminoacid sequences: Ag1: valine (or alanine), alanine, glutamic acid, alanine (orthreonine), glutamic acid, lysine, glutamine, lysine (or arginine), alanine, alanine, glutamic acid, alanine (or serine), threonine (or methionine or alanine) and lysine. Ag2: methionine, glutamic acid, glutamine, glutamic acid arginine, arginine, glutamine, leucine, leucine, glutamic acid, lysine, aspartic acid, proline, arginine, arginine, asparagine, alanine, lysine, glutamic acid, isoleucine alanine, alanine, leucine, glutamic acid, glutamic acid, serine, methionine, asparagine, alanine, arginine, alanine, glutamine, glutamic acid, leucine, alanine, arginine, glutamic acid, lysine, lysine, leucine, arginine, aspartic acid, arginine, alanine, phenylalanine, leucine, aspartic acid, glutamine, lysine, proline, glutamic acid, arginine, valine, proline, leucine, alanine, aspartic acid, valine, proline, leucine, aspartic acid, aspartic acid, aspartic acid, serine, aspartic acid, phenylalanine, valine and alanine.

4 Claims, 1 Drawing Sheet

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Val Xaa Ala Glu Ala Xaa Glu Lys Gln Lys Xaa Ala Ala Glu Ala Xaa
 1               5                  10                  15

Thr Xaa Xaa Lys
                20
```

( 2 ) INFORMATION FOR SEQ ID NO:2:

( i ) SEQUENCE CHARACTERISTICS:
        ( A ) LENGTH: 68 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Met Glu Gln Glu Arg Arg Gln Leu Leu Glu Lys Asp Pro Arg Arg Asn
 1               5                  10                  15

Ala Lys Glu Ile Ala Ala Leu Glu Glu Ser Met Asn Ala Arg Ala Gln
                20                  25                  30
```

```
Glu Leu Ala Arg Glu Lys Lys Leu Arg Asp Arg Ala Lys Leu Asp Gln
        35                  40                  45

Lys Pro Glu Arg Val Pro Leu Ala Asp Val Pro Leu Asp Asp Asp Ser
    50                  55              60

Asp Phe Val Ala
65
```

METHOD FOR THE IMMUNOLOGICAL DIAGNOSIS OF CHAGAS' DISEASE USING RECOMBINANT ANTIGENS

This is a continuation of application Ser. No. 07/916,073, filed as PCT/BR91/00027 Nov. 28, 1991, published as WO92/09895 Nov. 6, 1992, which was abandoned upon the filing hereof.

BACKGROUND OF THE INVENTION

This patent request refers to the use of antigens conjugated to an enzymatic activity (detectable by color reaction), in diagnostic assays for Chagas' disease and other infectious diseases.

The methods generally used for the serological diagnosis of infectious diseases rely on the presence of antibodies against the pathogen in the sera of the infected patient. But these techniques can present some limitations in their specificity when crude antigen preparations are used. On the other hand, the use of purified antigens can present problems in terms of cost and large scale applicability. However, the development of recombinant DNA techniques paved the way to the large scale obtension of purified antigens with lower cost and safer conditions. Accordingly, our work with *Trypanosoma cruzi* (the etiological agent of Chagas' disease), resulted in the cloning and expression in bacteria of antigens from the parasite that are specifically recognized by chagasic sera.

The ELISA test (enzyme linked immunoenzymatic assay) is frequently used for serological diagnosis. This method allows the identification and quantification of antigens or antibodies in biological fluids. The conventional ELISA consists in the detection of the complex antibody-antigen by a second antibody (against the antibody that reacts with the antigen) conjugated to an enzymatic activity (peroxidase, alkaline phosphatase and others).

Alternatively, the immune-complex can be also detected using *Staphglococcus aureus* protein-A or protein-G conjugated to the enzymatic activity. However, this conventional ELISA does not detect low titer antibodies, resulting in the failure to distinguish among positive and negative sera. In the case of the use of recombinant antigens, this problem can be amplified in virtue of the cross-reactivity with bacterial antigens that can eventually contaminate the preparation.

A method based on the detection of highly specific antibodies (irrespective to their titre) should avoid the limitations of the ELISA test described above. This can be performed by using the antigen to sensitize the ELISA support and to develop the immune-complex through its conjugation to the enzymatic activity or radioactive labelling.

BRIEF DESCRIPTION OF THE DRAWINGS

Further objects and advantages of the present invention will be better understood by carefully reading the following description of the presently preferred exemplary embodiments of this invention in conjunction with the accompanying drawings, of which.

Figure 2:
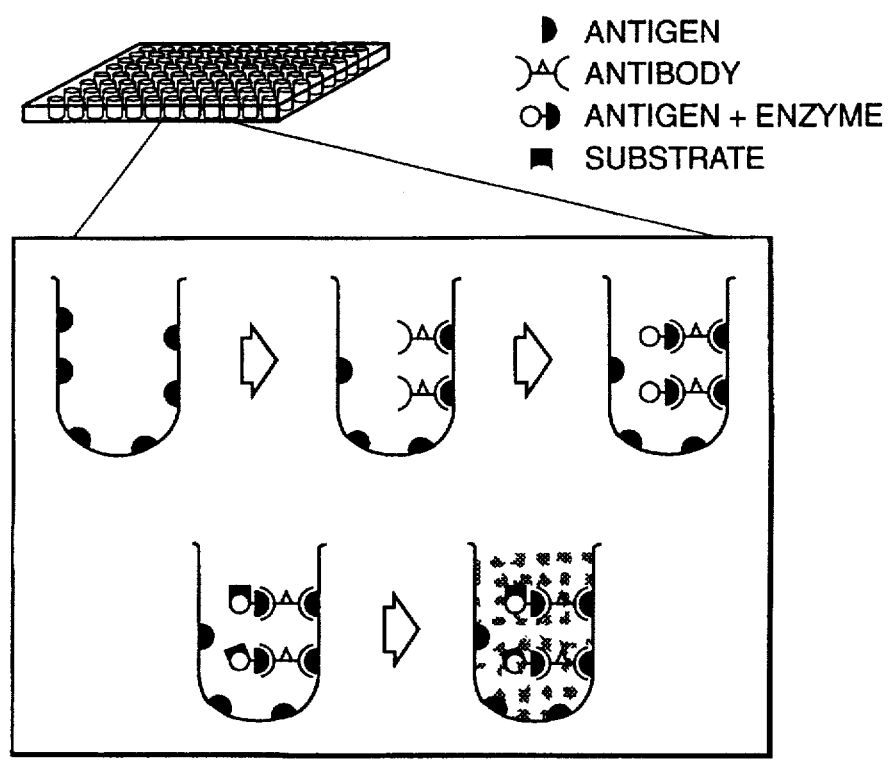
FIG. 2 is a graphical representation of a direct ELISA.

This patent application refers to the development of a direct ELISA and its use in the diagnosis of Chagas' disease. This method relies on the use or the antigen for sensitizing the plate and for the detection of the immune-complexes. The method, which is graphically represented in the scheme of FIG. 2, is fast and allows the visual reading of the result.

Figure 1:
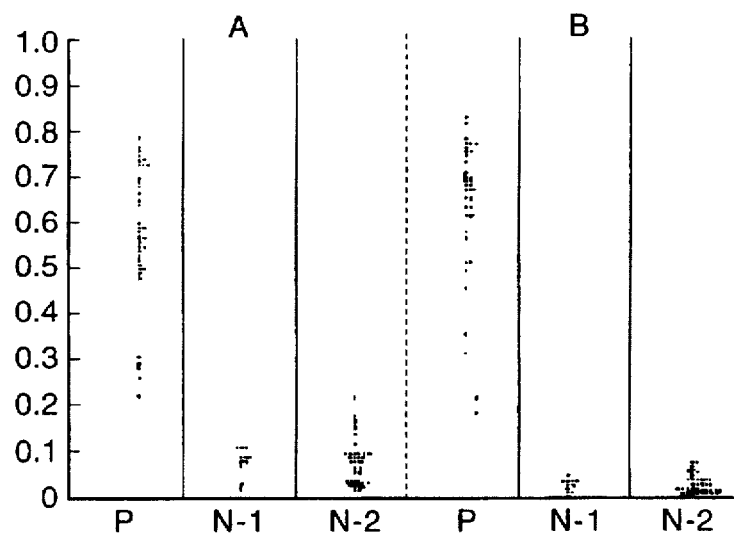
FIG. 1 shows results of using a conventional ELISA (part A) and direct ELISA (part B)

Some results using the direct ELISA and the comparison with a conventional ELISA are described below. The results presented in FIG. 1 compare the reactivity of human chagasic sera (lane P), non-chagasic sera from endemic areas (lane N-1) and non-chagasic sera from blood bank (N-2) using a conventional ELISA (FIG. 1, Part A) and the direct ELISA (FIG. 1, part B). It can be observed that the cut-off line is much more clear in the case of the direct than in the case of the indirect ELISA. The results presented in Table I compare the reactivity of the direct and the indirect ELISA with different human sera. The direct ELISA is much more specific and sensible than the conventional ELISA since no false positive or false negative results were observed using this method.

DESCRIPTION OF THE INVENTION

The procedures of the method are as follows. The antigen or antigenic mixture, in a concentration ranging from 0.01 to 1 mg/ml, depending on the antigen, is immobilized in the solid support. The antigen is diluted in 50 mM carbonate buffer, phosphate buffer or any other suitable buffer for immobilization to the support, which can be polycarbonate, polyallomer, polypropylene, polyvinyl, nylon and nitrocellulose. The solid phase sensitized with the antigen is washed with phosphate buffered saline pH 7.0–7.5 containing 0.3% detergent, and dried out. The sera to be analysed are applied onto the support containing the antigen and the ensemble is incubated at 25°–37° C. for times varying from 30 minutes to 120 minutes.

Following this, the solid phase is washed with phosphate buffered saline or any other suitable buffer.

The immune-complexes are developed with the total or fractions of the antigenic mixture used to sensitize the support, conjugated to an enzymatic activity or radioactively labelled. The conjugated antigen is diluted in phosphate buffered saline, or any suitable buffer, containing a blocking agent such as gelatin, bovine sera, BSA, milk, etc., in order to avoid non-specific binding to the support. After incubation at 37° C., the immune-complexes are developed according to the enzymatic reaction suitable for the conjugated enzyme or radioactive labelling.

Two kits for the diagnosis of Chagas' disease were developed based on the procedures described above: a direct ELISA kit and a kit using a membrane (nylon or nitrocellulose) as support. The Direct ELISA kit is composed of a micro-titre plate coated with the antigens (described in the International Application under the Patent Cooperation Treaty PCT/BR 91/00003, Brazilian Application number 9001479) in a concentration of 0.1 mg/ml, a flask containing the conjugated antigen, three tubes containing control sera that consist of negative, positive and cut-off sera, a flask with washing buffer (buffered saline solution, pH7.5, containing 0.3% Tween——20), washing buffer containing foetal bovine sera 5% and the solutions necessary for developing the enzymatic reaction. The antigens described in PCT/BR 91/00003 are the following, as defined by their amino acid sequence:

Antigen #1 (SEQ ID NO:1)

Valine (or alanine), alanine, glutamic acid, alanine (or threonine), glutamic acid, lysine, glutamine, lysine (or arginine), alanine, alanine, glutamic acid, alanine (or serine), threonine (or methionine or alanine) and lysine.

Antigen #2 (SEQ ID NO:2)

Methionine, glutamic acid, glutamine, glutamic acid, arginine, arginine, glutamine, leucine, leucine, glutamic acid, lysine, aspartic acid, proline, arginine, arginine, asparagine, alanine, lysine, glutamic acid, isoleucine, alanine, alanine, leucine, glutamic acid, glutamic acid, serine, methionine, asparagine, alanine, arginine, alanine, glutamine, glutamic acid, leucine, alanine, arginine, glutamic acid, lysine, lysine, leucine, arginine, aspartic acid, arginine, alanine, phenylalanine, leucine, aspartic acid, glutamine, lysine, proline, glutamic acid, arginine, valine, proline, leucine, alanine, aspartic acid, valine, proline, leucine, aspartic acid, aspartic acid, aspartic acid, serine, aspartic acid, phenylalanine, valine and alanine. The kit also contains an explanatory note on how to proceed. Briefly, the sere to be tested (undiluted or diluted until 1:200) in a volume of 50 μl are put in the well and incubated for 30–60 minutes at 37° C. and then removed. The wells are washed three times with washing solution as described above and then, the antigen conjugated to the enzymatic activity diluted 1:1000 is added in a final volume of 50 μl and incubated at 37° C. for 60 minutes. The wells are washed three times with washing buffer and then the substrate of the enzyme is added (3,3',5,5'-tetramethyl benzidine 0.01 mg/ml in DMSO and 0.3% hydrogen peroxide in the case of peroxidase). Following 10 minutes of incubation at room temperature, the reaction is stopped by the addition of 4M sulphuric acid. The results can be read visually or in the spectrophotometer by the absorbance at 450 nm.

In the case of the kit using a solid support (nitrocellulose, nylon, polyallomer, polycarbonate, polyvinyl, etc.), the antigens are spread onto the membrane and their position is signaled. The strips are then placed inside a tube that is the reaction vessel. The kit contains 20 tubes with strips, the conjugate solution, control sera and washing buffer consisting of phosphate buffered saline solution (pH 7.5) containing 0.3% Tween——20. In addition, the kit contains a dilution solution (washing butter containing 5% bovine serum) and the reagents necessary for developing the enzymatic reaction, described above. The serum sample to be tested is diluted 1:100 in washing solution and 2 ml of this solution are put inside the reaction tube containing the membrane.

After incubation at 37° C. for 60 minutes, the serum is removed and the strip is washed three times with 2 ml of washing solution. Following this, the conjugate in a final volume of 2 ml and in a dilution of 1:1000 is added to the reaction vessel containing the strip, and incubated for additional 60 minutes at 37° C. The conjugate is removed, the strip is washed twice with washing buffer and the substrate of the enzyme is added. The reaction proceeds for 10 minutes and is then stopped with water. The result of the reaction is determined by the intensity of the color respective to the controls.

These kits are stable for at least six months at 4° C. and for one month at 37° C. The conjugate is kept in physiological saline solution containing 20% glycerol and proteinase inhibitors.

---

We claim:

1. A method for the immunological diagnosis of Chagas' disease comprising the following steps:
   (i) sensitizing a support of a material selected from the group consisting of polycarbonate, polyallomer, polypropylene, polyvinyl, nylon or nitrocellulose with a 50 mM carbonate buffer containing 0.01 to 1.0 mg/ml of a mixture of the Antigen #1 (SEQ ID NO:1) and Antigen #2 (SEQ ID NO:2);
   (ii) washing the sensitized support with a washing buffer of a phosphate buffered saline (PBS) pH 7.0 with 0.3% of detergent;
   (iii) adding to the ensemble of the step (ii) the serum to be tested and incubating the ensemble for a sufficient time to permit the specific binding between the antigens Antigen #1 (SEQ ID NO:1) and Antigen #2 (SEQ ID NO:2), and antibodies to *Trypanosoma cruzi;*
   (iv) washing the ensemble which contains the serum with the same buffer solution used in the step (ii);
   (v) preparing a solution comprising enzyme-conjugated Antigen #1 (SEQ ID NO:1) and enzyme-conjugated Antigen #2 (SEQ ID NO:2), said enzymes having an enzymatic activity;
   (vi) diluting the solution comprising enzyme-conjugated Antigen #1 (SEQ ID NO:1) and enzyme-conjugated Antigen #2 (SEQ ID NO:2) to block nonspecific binding sites, said diluting solution consisting of the washing buffer which contains 5% of bovine sera;
   (vii) adding to the ensemble of step (iv) the solution of the step (vi) and incubating for a sufficient time to permit the interaction between the antibodies to *Trypanosoma cruzi* and the antigens having an enzymatic activity;
   (viii) effecting the development of immunocomplex by adding to the ensemble of step (vii) the substrate solution and then incubating for a sufficient time to permit the interaction between the enzyme and the substrate;
   (ix) blocking the enzymatic activity by addition of a stop solution; and
   (x) evaluating the results of the enzymatic activity in relation to a standard serum.

2. The method according to claim 1 wherein the step (iii) is carried out at room temperature between 25° C. to 37° C., in a period of time from 30 minutes to 2 hours.

3. The method according to claim 1 wherein the step (vii) is carried out at room temperature between 25° C. to 37° C., during 30 minutes.

4. The method according to claim 1 wherein the step (viii) is carried out at room temperature between 25° C. to 37° C., during 10 minutes.

* * * * *